US00PP08083P

United States Patent [19]

Lyrene

[11] Patent Number: Plant 8,083

[45] Date of Patent: Jan. 5, 1993

[54] RABBITEYE BLUEBERRY CULTIVAR WINDY

[75] Inventor: Paul M. Lyrene, Gainesville, Fla.

[73] Assignee: University of Florida Research Foundation, Inc., Gainesville, Fla.

[21] Appl. No.: 640,192

[22] Filed: Jan. 10, 1991

[51] Int. Cl.[5] ..... A01H 5/00

[52] U.S. Cl. ..... Plt./33.1

[58] Field of Search ..... Plt./33, 33.1

[56] References Cited

U.S. PATENT DOCUMENTS

P.P. 6,701 3/1989 Wood ..... Plt. 33

*Primary Examiner*—James R. Feyrer

*Attorney, Agent, or Firm*—Saliwanchik & Saliwanchik

[57] ABSTRACT

Description and specifications of a new and distinct rabbiteye blueberry variety which originated from seed produced by a hand-pollinated cross of Florida 79-19 and Florida 79-27 is provided. The new rabbiteye blueberry variety can be distinguished from all others by its low chilling requirement, its early flowering, and its early ripening, and by its high-quality fruit that can be mechanically harvested for the fresh market.

1 Drawing Sheet

SUMMARY OF THE INVENTION

The new and distinct variety of rabbiteye blueberry originated from a hand pollinated cross of Florida selection 79-19×Florida selection 79-27 made in 1980 at the Florida Agricultural Experiment Station blueberry breeding greenhouse in Gainesville, Fla. The seeds resulting from this controlled hybridization were germinated in a greenhouse during the winter of 1980–1981. Resulting seedlings were planted in the spring of 1981 in a field on the University of Florida Horticultural Unit at Gainesville, Fla. The seedlings fruited in the spring of 1983 and one, designated FL 83-97, was selected for its outstanding fruit quality and early ripening, as compared to other known varieties.

During 1983, the original plant selection was propagated asexually by rooting softwood cuttings, and a test planting of 15 bushes was established at the Horticultural Unit. This plot has been observed each year since its establishment at various seasons of the year, and data have been collected to document the important plant and fruit characteristics. Other rooted cuttings of this clone have been pollinated at the University of Florida blueberry breeding greenhouse to obtain information on fertility and fruit quality under greenhouse conditions.

The new variety has been asexually propagated on at least five occasions by softwood cuttings. It roots readily from softwood cuttings and grows well in the cuttings nursery. In all cases in which the clone has been propagated by cuttings, the vegetative and fruit characteristics of the original plant have been maintained.

Bushes of the new variety are vigorous and upright in growth. Plants set on a soil of intermediate fertility were 190 cm after six years. Sprouts from the plants were arising from a band 120 cm wide from six-year old plants and the drip line of the canopy was 220 cm wide. The plant produces basal shoots in sufficient quantities to renew the plant as it ages. Because Windy prolifically sprouts from the base by means of rhizome budding, pruning or mowing will be needed to maintain the narrow base necessary for mechanical harvesting. After six to eight years, top hedging or selective cane removal is needed to prevent excessive plant height. The number of flower buds produced is about average for rabbiteye blueberry varieties and is sufficient to produce a heavy crop. Plants of the new variety flower one week before they produce new leaves in the spring, and foliation has always been excellent.

Plants of the new variety appear to be above average for a rabbiteye blueberry in tolerance to Phytophthora root rot. Neither can canker, incited by *Botryosphaeria corticus,* nor stem blight, incited by *Botryosphaeria dothedia,* has been a problem in the field plantings. Resistance to Botrytis blight, incited by *Botrytis cinerea,* has been equal to or greater than that of most other rabbiteye cultivars planted in the same test plots. Leaf retention is good in the fall, indicating satisfactory levels of tolerance to the various species of defoliating fungal pathogens prevalent in the experimental area.

The new variety is very low in chill requirement, and has flowered within a few days of the early-flowering cultivars Aliceblue, Beckyblue, and Climax each year. These varieties are recommended to provide cross-pollination for Windy. The fruit ripen exceptionally early for a rabbiteye blueberry. Over a 4-year period during which flowering dates were compared, the new variety averaged 8.3 days earlier in ripening than Beckyblue, which is the earliest-ripening rabbiteye cultivar now available, and 14.5 days earlier than Climax, another rabbiteye variety widely grown because of its early ripening. The average date of first commercial harvest on plants of the new variety grown in north central Florida will be about May 10, and midharvest will be about May 18. Harvest dates are about ten days later than for the highbush variety Marimba.

Fruit of the new variety are large, medium-blue in color, with a medium waxy bloom. Flavor is very similar to that of the major rabbiteye varieties. Seediness and skin thickness are about average for a rabbiteye blueberry cultivar. The fruit detach readily from the plant when ripe, the stem scar is relatively small and dry, and the berries have medium to good firmness. Therefore the variety is expected to be satisfactory for mechanical harvest under normal weather conditions. The calyx on the fruit just prior to final swell distinguishes Windy from both Marimba and Snowflake. The calyx cup is very shallow for Windy (about 1 mm deep) whereas the calyx cups on Marimba and Snowflake berries average about 4 mm deep.

Windy has 72 chromosomes in each somatic cell and is distinguished from Marimba which has 48 chromosomes in each somatic cell.

The new variety has been named the WINDY cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject blueberry clone. Where dimensions, sizes, colors, and other characteristics are given, it is to be understood that such characteristics are approximations of averages set forth as accurately as practicable.

The description reported herein is from specimens grown at Gainesville, Fla.

Plant:

*Size.*—Medium: 190 cm tall and sprouting from a base 120 cm in diameter after six years in field plots.

*Time of* 50% *anthesis.*—Feb. 27.

*Growth.*—Medium to high vigor, cessation of growth in early October. Plant more upright than spreading.

*Productivity.*—Medium. Young plants precocious.

*Cold hardiness.*—Plant and dormant flower buds hardy to below −13° C. Flowers and fruits hardy to −2° C.

*Chilling requirements.*—The plant requires only 300 hours duration of temperatures at or below 7° C. to induce normal leafing and flowering in the spring.

*Stems.*—Moderately upright. Readily produces new sprouts from rhizomes. On six-year old plants growing in the field, length of the terminal growth in one season is 30 cm for mature stems and 100 cm for renewal stems.

*Internode length.*—1.1 cm. Color of 1-year-old steme — orange (2I, Plate 20 in Maerz, A. and M. R. Paul (1950) "A Dictionary of Color", 2d Ed.).

*Disease resistance.*—Moderate resistance to Phytophthora root rot, stem blight, powdery mildew, Botrytis flower blight, and various defoliating leaf diseases. High resistance to cane canker.

Foliage:

*Leaves.*—Color — mature leaves green to blue-green (3D, Plate 28, Dictionary of Color, supra). Leaf margins serrulate. Leaves glabrous except for stalked glands along margins and on lower surface. Leaves average 25 mm wide×41 mm long.

Flowers:

*Date of* 50% *anthesis.*—February 27.

*Flower color.*—white.

*Flower shape.*—Urceolate. Mean corolla length: 9 mm; width: 7 mm; mean diameter of corolla tube aperture : 3 mm.

*Flower bud number.*—Medium. Mean number of flowers per cluster — 6.

The variety is highly self-incompatible.

Fruit:

*Maturity.*—First harvest May 10. Mid harvest May 18.

*Size of berry.*—Medium large. Average weight 1.70 g. Calyx cup 1 mm deep. Berry averages 11 mm tall and 13 mm in diameter.

*Berry color.*—Dark blue (7A, Plate 45, Dictionary of Color, supra), with moderate surface wax.

*Fruit stem scar.*—Medium good. Some skin tearing on a small fraction of the berries.

*Berry firmness.*—Medium good. Firmer than the cultivar Premier but not as firm as Climax.

*Berry flavor and texture.*—Flavor sweet with moderate acid level. Skins of normal thickness and seeds of normal size and number for rabbiteye cultivars.

*Storage quality.*—Medium to good.

*Uses.*—Primarily for fresh shipping market. Also suitable for customer-pick and process market.

*Suitability for mechanical harvest.*—Medium to good.

The Variety

The most distinctive feature of the variety is its time of ripening. The variety ripens 8 to 14 days earlier than the earliest-ripening rabbiteye blueberry variety previously available. It produces a high-quality fruit that can be machine harvested for the fresh market.

I claim:

1. A new and distinct variety of rabbiteye blueberry plant, substantially as illustrated and described, characterized by its early ripening, vigorous, disease-resistant bush, low chilling requirement, and berry that can be mechanically harvested for the fresh market..

* * * * *

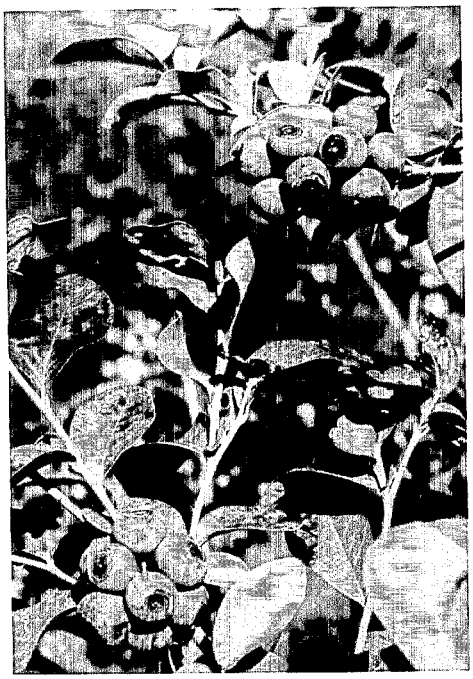
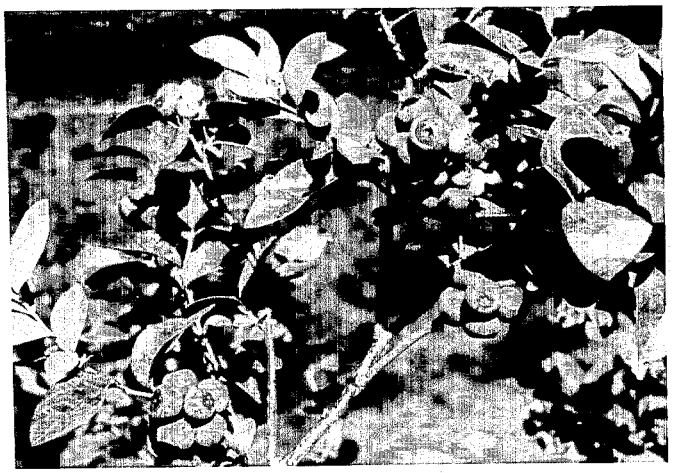

UNITED STATES PATENT AND TRADEMARK OFFICE

CERTIFICATE OF CORRECTION

PATENT NO. : Plant 8, 083
DATED : January 5, 1993
INVENTOR(S) : Paul S. Lyrene

It is certified that error appears in the above-indentified patent and that said Letters Patent is hereby corrected as shown below:

Column 3, line 50, "Maerz" should read --Maertz--.

Signed and Sealed this

First Day of February, 1994

*Attest:*

*Attesting Officer*

BRUCE LEHMAN

*Commissioner of Patents and Trademarks*